United States Patent [19]
Hasson

[11] Patent Number: 5,984,948
[45] Date of Patent: Nov. 16, 1999

[54] DEVICE FOR CLOSING AN OPENING IN TISSUE AND METHOD OF CLOSING A TISSUE OPENING USING THE DEVICE

[76] Inventor: Harrith M. Hasson, 2043 N. Sedgwick, Chicago, Ill. 60614

[21] Appl. No.: 09/082,932

[22] Filed: May 21, 1998

Related U.S. Application Data

[63] Continuation-in-part of application No. 08/824,699, Apr. 14, 1997, Pat. No. 5,830,232.

[51] Int. Cl.$^6$ .................................................. A61B 17/04
[52] U.S. Cl. ........................... 606/213; 606/144; 606/148
[58] Field of Search .................................. 606/213, 144, 606/148, 139

[56] References Cited

U.S. PATENT DOCUMENTS

| | | | |
|---|---|---|---|
| 5,021,059 | 6/1991 | Kensey et al. | 606/213 |
| 5,306,290 | 4/1994 | Martins et al. | 606/232 |
| 5,391,173 | 2/1995 | Wilk | 606/144 |
| 5,413,571 | 5/1995 | Katsaros et al. | 606/213 |
| 5,486,195 | 1/1996 | Myers et al. | 606/213 |
| 5,531,759 | 7/1996 | Kensey et al. | 606/213 |
| 5,540,715 | 7/1996 | Katsaros et al. | 606/13 |
| 5,545,178 | 8/1996 | Kensey et al. | 606/213 |
| 5,601,577 | 2/1997 | Hasson | 606/148 |
| 5,871,474 | 2/1999 | Hermann et al. | 604/256 |

OTHER PUBLICATIONS

"A Simple Technique for the Closure of Laparoscopic Trocar Wounds" Journal of the American College of Surgeons, Dec. 1995, vol. 18, p. 565.

*Primary Examiner*—Gary Jackson
*Attorney, Agent, or Firm*—Wood, Phillips, VanSanten, Clark & Mortimer

[57] ABSTRACT

A device for facilitating the performance of a medical procedure in a cavity bounded by a tissue. The device has a body with a first opening therethrough to define a first passageway for a medical instrument to be directed from externally of the cavity through an opening in the tissue to the cavity, and an exposed surface that can be placed against the tissue around the opening therethrough with the device in an operative state relative to the tissue. A second opening through the body defines a second passageway through which a tying instrument can be directed from externally of the tissue through the body and into the cavity bounded by the tissue. A first repositionable element is movable between first and second positions relative to the body. In the first position, the first repositionable element allows a suturing thread to be placed into and removed from a holding position. In the second position, the first repositionable element captively maintains a suturing thread in the holding position.

21 Claims, 10 Drawing Sheets

DEVICE FOR CLOSING AN OPENING IN TISSUE AND METHOD OF CLOSING A TISSUE OPENING USING THE DEVICE

CROSS-REFERENCE

This application is a continuation-in-part of application Ser. No. 08/824,699 filed Apr. 14, 1997, now U.S. Pat. No. 5,830,232, entitled "Device for Closing an Opening in Tissue and Method of Closing a Tissue Opening Using the Device".

BACKGROUND OF THE INVENTION

1. Field of the Invention

This invention relates to medical instruments and procedures and, more particularly, to a medical device that can be used to assist the performance of an internal medical procedure and/or the closing of a tissue opening and a method of using this device.

2. Background Art

Many of the procedures performed by open laparotomy are currently performed by operative laparoscopy. With increased applications of advanced operative laparoscopy, surgeons are experiencing an increased incidence of herniations through laparoscopy sleeved cannula sites. To prevent this complication there is a developing consensus to close the surgical defect associated with the insertion of laparoscopy cannulas 10 mm or greater in outside diameter. Although rare, sliding hernias have been reported with 5 mm laparoscopy cannulas.

Numerous needles and other devices have been developed to accomplish full thickness closure of the abdominal wall at the operative site of cannula insertion. However, the use of such devices has been associated with a certain degree of difficulty. If the device is used while the cannula is still in place, it is cumbersome to introduce the device between the cannula and the skin, because the cannula is tightly apposed to the skin margins of the incision. This is done to penetrate the abdominal wall excluding the skin. Furthermore, obtaining a suitable tissue purchase i.e. further away from the edge of the fascial defect, is technically difficult. On the other hand, if the cannula is tilted within the incision to improve access to the deeper layers of the abdominal wall, the pneumoperitoneum gas escapes rapidly through the less than tight application. Loss of the pneumoperitoneum gas makes the process of penetrating the abdominal wall with a sharp object extremely dangerous; because the bowel becomes quickly situated immediately under the abdominal wall. Therefore, this process has to be accomplished very quickly, without regard to accurate device placement within the abdominal wall.

If the closing device is applied after the laparoscopy cannula has been removed, the pneumoperitoneum gas escapes very rapidly through the open incision precluding any chance of a full thickness closure. Therefore, a device with a plug must be used to seal the incision and maintain the pneumoperitoneum while placing the full-thickness closing sutures.

SUMMARY OF THE INVENTION

The invention is directed to a device for facilitating the performance of a medical procedure in a cavity bounded by a tissue. The device has a body with a first opening therethrough to define a first passageway for a medical instrument to be directed from externally of the cavity through an opening in the tissue to the cavity, and an exposed surface that can be placed against the tissue around the opening therethrough with the device in an operative state relative to the tissue. A second opening through the body defines a second passageway through which a tying instrument can be directed from externally of the tissue through the body and into the cavity bounded by the tissue. A first repositionable element is movable between first and second positions relative to the body. In the first position, the first repositionable element allows a suturing thread to be placed into and removed from a holding position. In the second position, the first repositionable element captively maintains a suturing thread in the holding position.

The first repositionable element may be threaded so that it is pivotable about an axis in changing between the first and second positions.

In one form, the body has a first cantilevered arm defining a first surface and the first repositionable element has a second surface. The first and second surfaces are spaced from each other a first distance with the first repositionable element in the first position and the first and second surfaces are at least one of a) abutted to each other and b) spaced from each other a second distance that is less than the first distance with the first repositionable element in the second position.

The body may have a second cantilevered arm and a second repositionable element that cooperate with each other in the same manner as the first cantilevered arm and first repositionable element cooperate with each other.

In one form, the first passageway has a central axis and the first and second cantilevered arms project diametrically oppositely away from the central axis of the first passageway.

A releasable locking mechanism may be provided for releasably fixing a medical instrument directed through the first opening relative to the body.

The locking mechanism may have a ring member which extends at least partially around the first opening and bounds at least a part of the first opening.

In one form, the ring member has an effective diameter and the releasable locking mechanism includes a repositionable actuator that is movable between third and fourth positions. The ring member has a first effective diameter with the actuator in the third position and a second effective diameter that is less than the first effective diameter with the actuator in the fourth position. The ring member with the second effective diameter is capable of closely embracing a medical instrument directed through the first opening.

The repositionable actuator may be threaded so that it is pivotable about an axis in changing between the third and fourth positions.

The ring member in the third position may extend through less than 360° around the first opening.

The device may be provided in combination with a medical instrument directed into the first opening in the body.

In one form, there is a third opening through the body to define a third passageway through which a tying instrument can be directed from externally of the tissue through the body and into the cavity bounded by the tissue.

The device may be provided in combination with a suturing thread directed through tissue bounding a cavity and held captively in the holding position by the first repositionable element.

A resilient sealing material may be provided through which the second opening is formed so that the resilient sealing material is directly exposed at the second opening.

In one form, the body has a first surface, the repositionable element has a second surface, the second surface on the first repositionable element captively maintains a suturing thread in its holding position with the repositionable element in the second position, and the exposed surface of the body and the first surface are formed together as a unitary structure.

The invention also contemplates the combination of a) a device for facilitating the performance of a medical procedure in a cavity bounded by a tissue and having a body with a first opening therethrough defining a first passageway and an exposed surface that can be placed against the tissue around the opening therethrough with the device in an operative state relative to the tissue, b) a medical instrument for performing a procedure within the cavity and directed from externally of the cavity through the first passageway into the cavity, and c) a suturing thread extending through the tissue and the body and held to the body to at least one of i) stabilize the body relative to the tissue and ii) facilitate tying of the suturing thread.

The combination may further include tissue against which the body is placed so that the body is in the operative state.

DETAILED DESCRIPTION OF THE DRAWINGS

Figure 1:
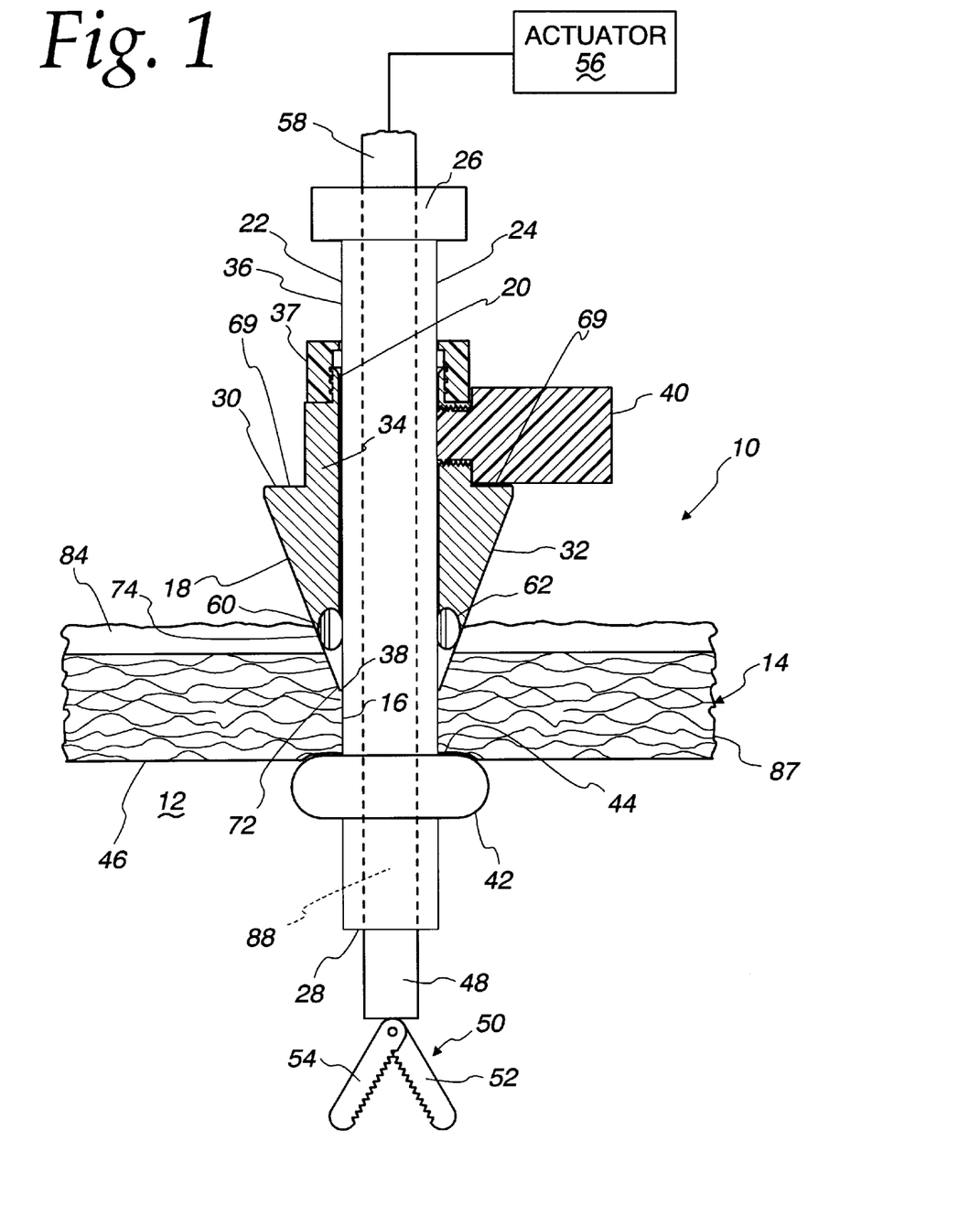
FIG. 1 is an elevation view, partially in cross-section, of one form of system for facilitating the performance of a medical procedure, according to the present invention, and with a device/sealing element in an operative state relative to tissue bounding a cavity and with a sleeve and medical instrument extending through the device/sealing element and into the cavity.
Figures 2, 3:
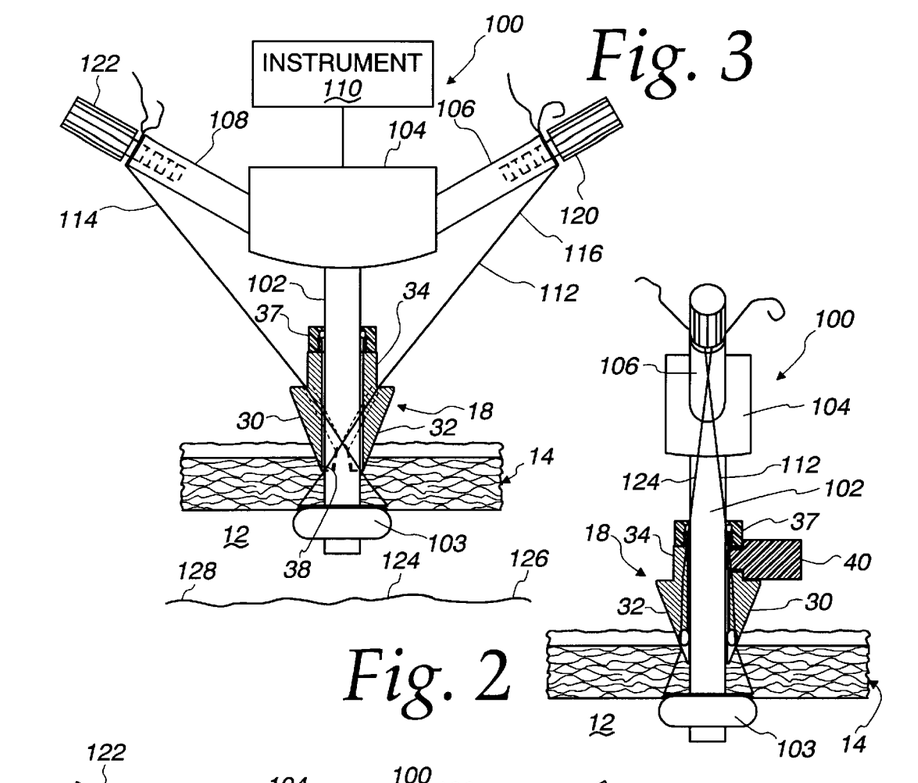
FIG. 2 is a view as in FIG. 1 of a modified form of system for facilitating the performance of a medical procedure, according to the present invention, and with a thread maintaining the device/sealing element stably in the operative state relative to the tissue.
FIG. 3 is an elevation view of the system in FIG. 2 rotated through 90° from the view in FIG. 2.
Figure 4:
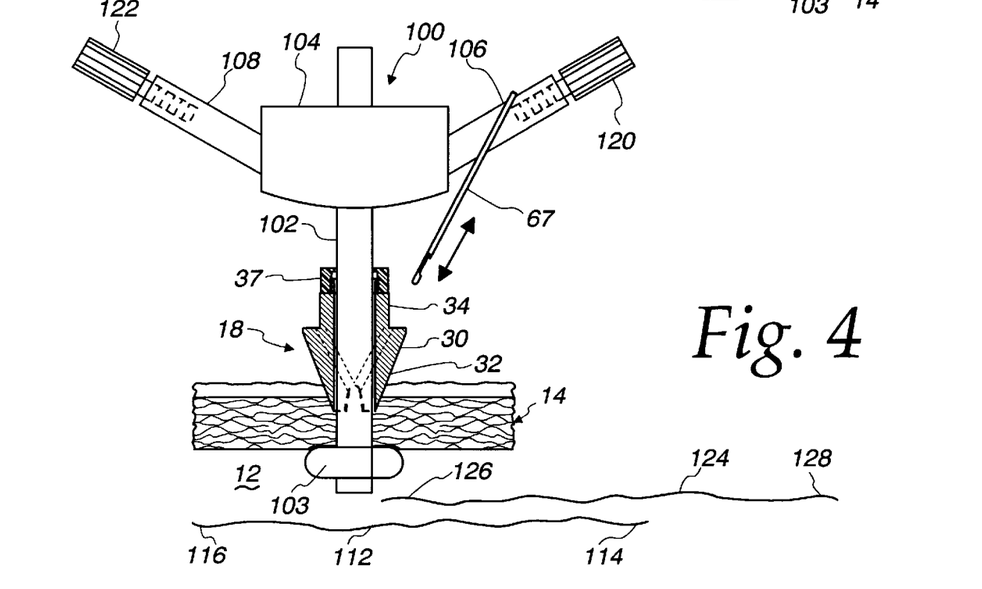
FIG. 4 is a view as in FIG. 2 with a tying instrument being directed through the device/sealing element to engage a thread within the cavity bounded by the tissue.

In FIG. 1, a system, according to the present invention, is shown at 10, for performing a procedure within a cavity 12 bounded by a tissue 14. The procedure is carried out through an opening 16 in the tissue 14. In a typical laparoscopic procedure, the opening 16 is on the order of 6–12 mm to accommodate instruments routinely used in laparoscopic procedures.

The system 10 includes a device/sealing element 18 with a first opening/passageway 20 therethrough to accommodate a cylindrical sleeve/cannula 22. The sleeve/cannula 22 has an inlet end 24 with a resilient sealing element 26 and an outlet end 28.

With the device/sealing element 18 and sleeve/cannula 22 in a relative operative position as seen in FIG. 1 and the device/sealing element 18 in the operative state as also shown in FIG. 1, the inlet end 24 of the sleeve/cannula 22 resides externally of the tissue 14, with the outlet end 28 residing within the cavity 12 bounded by the tissue 14.

As seen in FIGS. and 9–14, the device/sealing element 18 has a body 30 with a conical, external sealing surface 32. The body 30 has a neck 34 which closely surrounds the external surface 36 of the sleeve/cannula 22. A conventional, rubber seal 37 is press fit at the top of the neck 34 and closely embraces the sleeve/cannula 22. The bottom of the body 30 has an outlet opening 38 which closely receives the sleeve/ cannula 22. In a preferred form, the opening/passageway 20 has a uniform diameter substantially fully between the inlet and outlet ends of the body 30. With the sleeve/cannula 22 and body 30 in the relative operative position, the device/ sealing element 18 is slidable guidingly along the length of the sleeve/cannula 22. A hand operable set screw 40 is threaded through the neck 34 to against the sleeve/cannula 22. By tightening the set screw 40, the device/sealing element 18 can be fixed at any desired position along the length of the sleeve/cannula 22.

An inflatable bladder 42 surrounds the sleeve/cannula 22 adjacent to the outlet end 28 thereof. The bladder 42, in a deflated state, does not project significantly outwardly from the peripheral surface 36 of the sleeve/cannula 22. In an inflated state, as shown in FIG. 1, the bladder 42 defines an annular shoulder 44 surrounding the sleeve/cannula 22 which can be borne against the inwardly facing surface 46 of the tissue 14 as shown in FIG. 1.

To direct the sleeve/cannula 22 through the tissue 14, a sharpened trocar (not shown) is directed through the sleeve/ cannula 22. The bladder 42 is deflated. The trocar guides the outlet end 28 of the sleeve/cannula 22 through the preformed tissue opening 16 to the FIG. 1 position. The bladder 42 is then inflated, after which the sleeve/cannula 22 is drawn upwardly to bear the bladder shoulder 44 sealingly against the tissue surface 46. The device/sealing element 18 is then slid downwardly along the sleeve/cannula 22 into the operative state wherein the outlet end of the sealing surface 32 on the body 30 compresses the tissue 14 so that a seal is established between the surface 32 and the tissue 14 fully around the opening 16. At the same time, the tissue 14 becomes firmly captive between the device/sealing element 18 and the bladder 42 so that the sleeve/cannula 22 is stably maintained in 20 the FIG. 1 position on the tissue 14. This relationship is maintained by tightening the set screws 40.

Once the sleeve/cannula 22 and device/sealing element 18 are set up as in FIG. 1, a desired instrument can be directed through the sleeve/cannula 22 into the cavity 12. In this case, a forceps-type instrument 48 is shown having a working end 50 with relatively movable jaws 52, 54 that are operable through a remote actuator, shown schematically at 56 at a location externally of the cavity 12. The seal 26 surrounds the body 58 of the forceps 48 to prevent escape of gas from the cavity 12 as is typically used to distend the tissue 14 to provide an unobstructed working area at the outlet end 28 of the sleeve/cannula 22.

According to the invention, as seen in FIGS. 1 and 6–14, the body 30 of the device/sealing element 18 is provided with multiple, and in this case four, additional passageways 60, 62, 64, 66, each of which provides a guide path for an elongate, medical tying instrument. Two forms of a suitable medical tying instrument are shown at 67 and 68 in FIGS. 5 and 6. The instrument 67 has a conventional slot 69 which receives a suturing thread and can be used to either push or pull the thread through the tissue 12, depending upon which portion of the slot 69 is used. The instrument 68 has a conventional jawed construction. The particular configuration of the tying instrument is not critical to the present invention. Any medical tying instrument that can pass through the passageways 60, 62, 64, 66 into the cavity 12 with the system 10 in the FIG. 1 state can be employed.

In the embodiment shown, the passageways 60, 62, 64, 66 are substantially straight, with the central axes of the passageways 60, 62, 64, 66 being non-parallel. Exemplary passageway 60 extends through an upper annular surface 69 on the body 30 fully through the body 30 to an inverted, U-shaped cutout 70 adjacent to the bottom edge 72 of the body 30. As seen in FIG. 1, with the sleeve/cannula 22 and device/sealing element 18 in the relative operative position and the device/sealing element 18 in the operative state of FIG. 1, the outlet end 74 of the passageway 60 resides within, and preferably beneath, the outer skin layer 84 in the tissue 14 so that the central axis 86 of the passageway 60 passes through only a slight portion of the skin layer 84 and, more preferably, does not extend through the skin layer 84 at all. As a result, direction of one of the instruments 67, 68 through the passageway 60 causes the instrument 67, 68 to primarily or directly penetrate the layers 87 beneath the outer skin layer 84. The other passageways 62, 64, 66 are similarly configured and angled with respect to each other. Preferably the central axes of the passageways 60, 62, 64, 66 do not extend through the internal space 88 bounded by the sleeve/cannula 22.

Before describing the method of using the system 10, a modified form of system 100 as shown in FIGS. 2–5 will be described. The system 100 employs the device/sealing element 18, as previously described, and a sleeve/cannula 102 having an inflatable bladder 103 thereon. The sleeve/cannula 102 rigidly connects to an upper housing 104 which has two connecting arms 106, 108 projecting angularly away from the housing 104. This sleeve/cannula 102, housing 104, and connecting arm 106, 108 combination is shown in my U.S. Pat. No. 5,601,577, incorporated hereby by reference. An instrument shown schematically in FIG. 2 at 110, is directed through the housing 104, the sleeve/cannula 102, and into the cavity 12 in the same manner as the forceps 48 is directed through the sleeve/cannula 22 in FIG. 1. The device/sealing element 18 is fixed to the cannula 102 through the set screw 40 to maintain the sleeve/cannula 102 and device/sealing element 18 in the relative operative position in FIGS. 2–5.

The method of closing the tissue opening 16, according to the present invention, will now be described with reference to FIGS. 2–8, using the system 100. The system 10 is operable in essentially the same manner.

Figure 5:
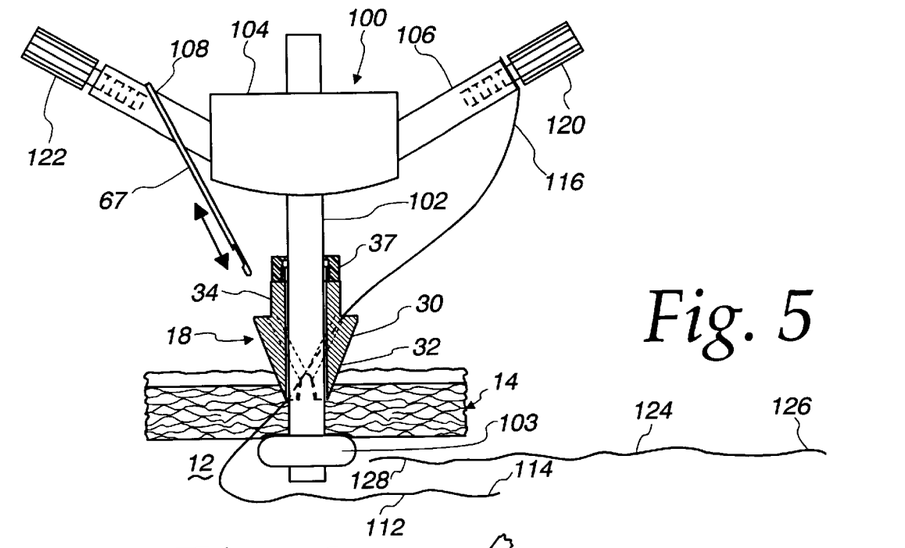
FIG. 5 is a view as in FIG. 4 with a part of the thread having been drawn through the device/sealing element.
Figure 6:
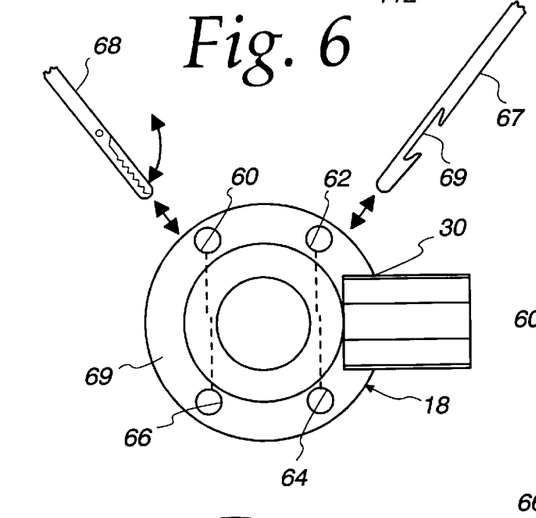
FIG. 6 is an enlarged, plan view of the inventive device/sealing element with different tying instruments being directed through passageways in the device/sealing element.
Figure 7:
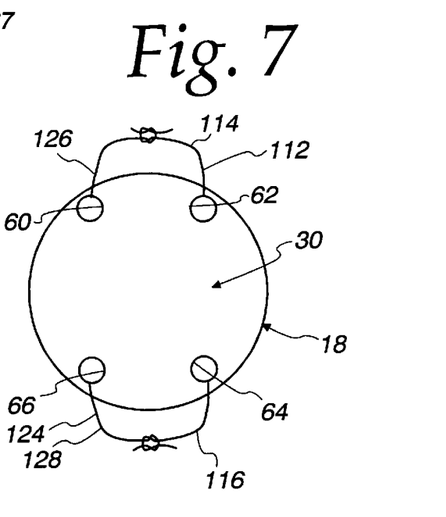
FIG. 7 is a schematic representation of the device/sealing element from the view as in FIG. 6 and showing one tying pattern for thread that is drawn through the device/sealing element.

With the sleeve/cannula 102 and the device/sealing element 18 in the relative operative position and the device/ sealing element 18 in the operative state of FIGS. 2–5, a suturing thread 112 is directed into the cavity 12. The thread 112 could be introduced into the cavity 12 before the system 100 is set up. Alternatively, using one of the instruments 67, 68, the thread 112 can be directed through one of the passageways 60, 62, 64, 66 with the system 100 set up. In FIG. 5, the thread 112 is directed through either of the passageways 64, 66. Thereafter, the instrument 67, 68 is directed through one of the passageways 60, 62 to engage the free end 114 of the thread 112 within the cavity 12 and draw the thread end 114 outwardly through the one of the passageways 60, 62.

The trailing end 116 of the thread 112 that remains outside of the cavity 12 is fixed to the arm 106 through a cap 120 which can be threaded into the connecting arm 106 to captively hold the thread end 116 thereagainst. The leading thread end 114 is then drawn taut and captively held against the other connecting arm 108 by threading a like cap 122 into the connecting arm 108. With this arrangement, the thread 112 serves to stabilize the sleeve/cannula 102 on the tissue 14. To add further stability, and also to facilitate closing of the tissue opening 16 as explained below, a separate thread 124 can be directed through the tissue 14 using the passageways 60, 62, 64, 66 not occupied by the thread 112 in the same manner as the thread 112. The ends 126, 128 of the thread 124 are secured to the connecting arms 106, 108 with the thread 124 drawn taut. The threads 112, 124 can cross each other as by extending through the openings 62, 66 or 60, 64 or remain uncrossed as by extending through the openings 60, 66 or 62, 64. Alternatively, the threads 112, 124 can extend through the openings 60, 62 or 64, 66.

With the system 100 set up as described above, the instrument 110, or any other desired instrument, can be positively controlled as the particular procedure is performed within the cavity 12. The threads 112,124 not only stabilize the sleeve/cannula 102 but inherently rigidify the tissue 14 around the working area.

Figure 8:
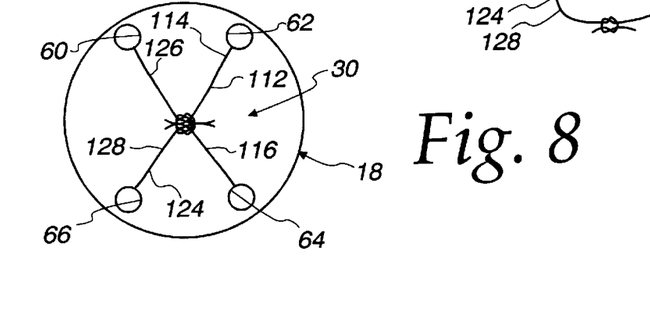
FIG. 8 is a view as in FIG. 7 showing another thread tying pattern.
Figure 9:
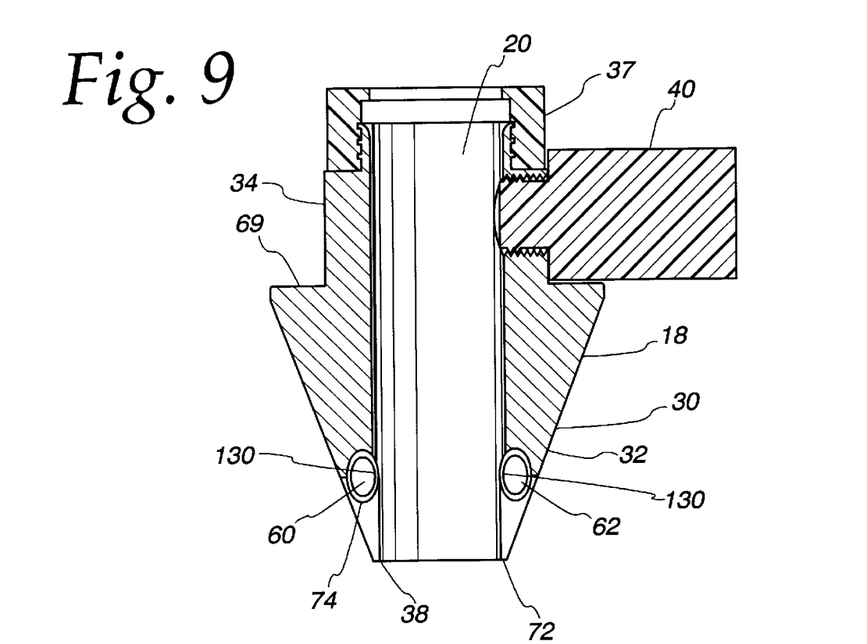
FIG. 9 is an enlarged, cross-sectional view of the inventive device/sealing element.
Figure 10:
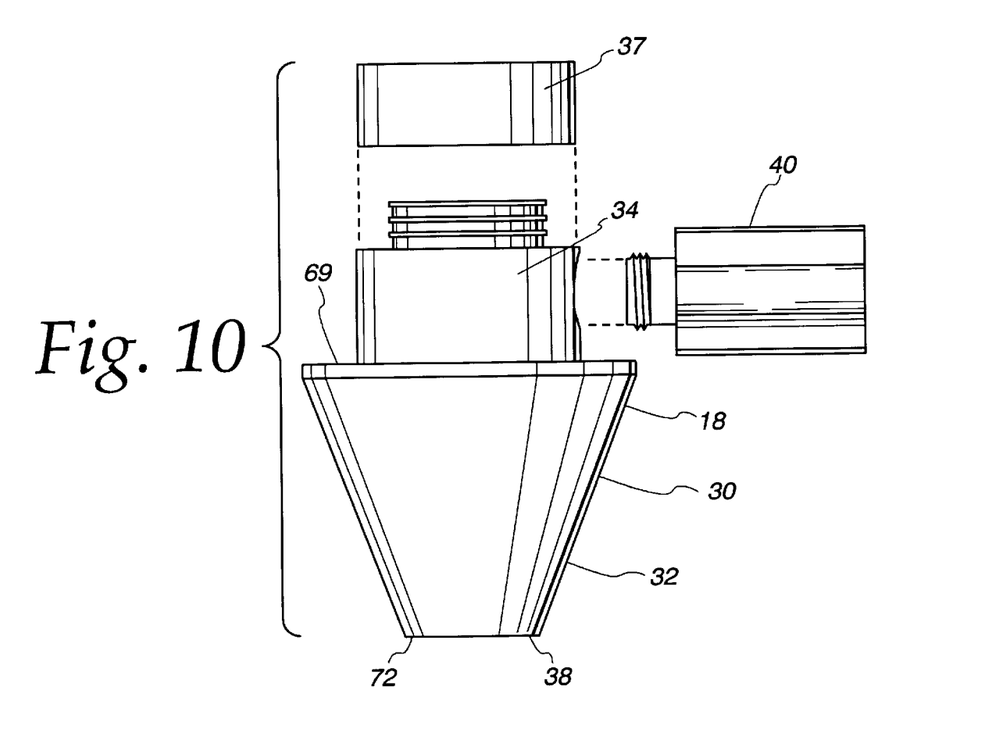
FIG. 10 is an enlarged, exploded, elevation view of the inventive device/sealing element.
Figure 11:
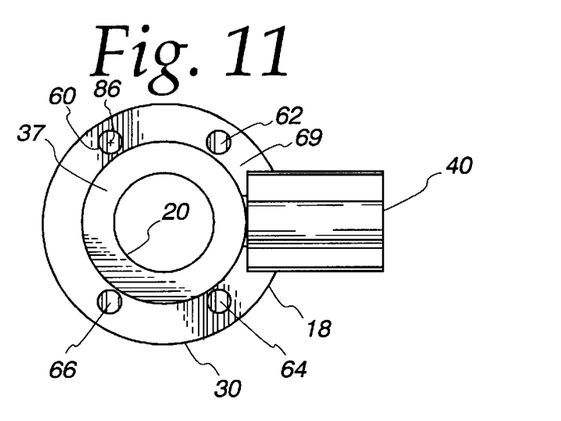
FIG. 11 is an enlarged, plan view of the inventive device/sealing element.
Figure 12:
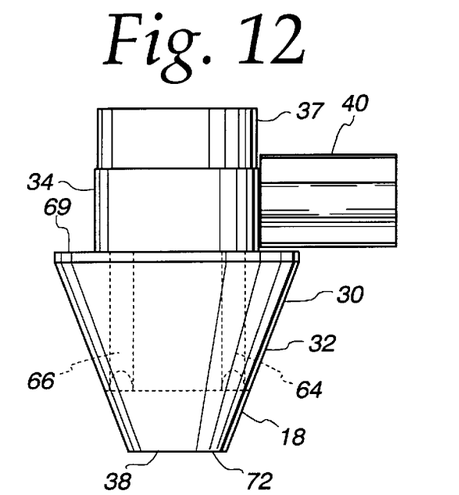
FIG. 12 is an enlarged, elevation view of the inventive device/sealing element.
Figure 13:
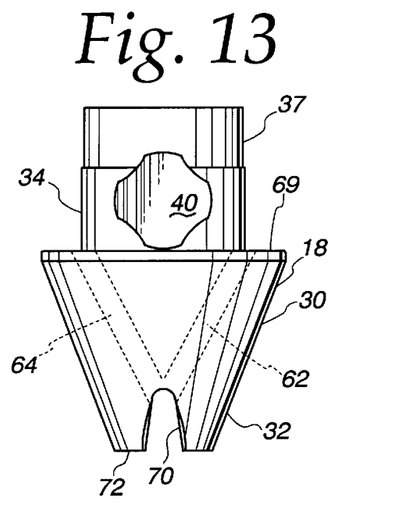
FIG. 13 is a view as in FIG. 12 with the device/sealing element rotated through 90° around a vertical axis from the view in FIG. 12.
Figure 14:
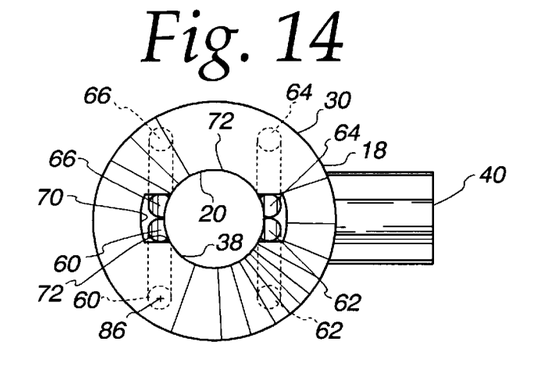
FIG. 14 is an enlarged, bottom view of the inventive device/sealing element.
Figure 15:
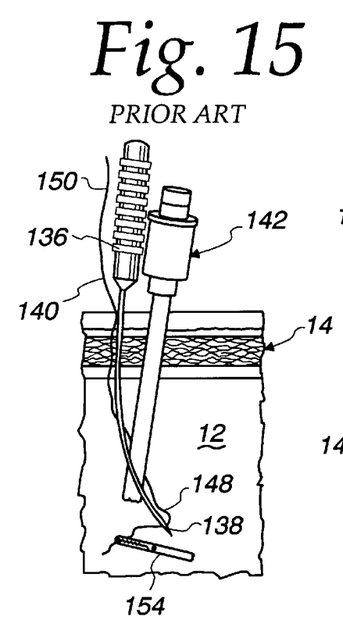
FIG. 15 is a schematic representation of a conventional suturing operation wherein a thread is directed by an instrument from externally of a tissue through the tissue and into a cavity.
Figure 16:
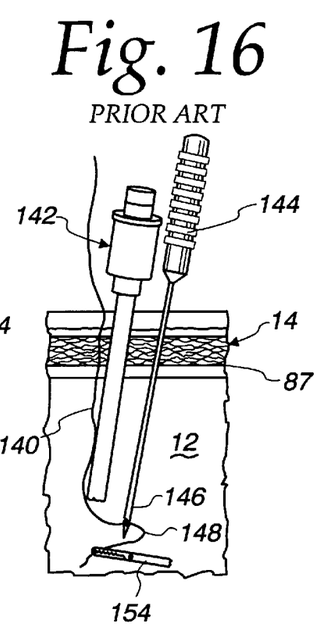
FIG. 16 is a view as in FIG. 15 wherein a separate instrument is used to engage and draw a portion of the thread in the cavity outwardly through the tissue.
Figure 17:
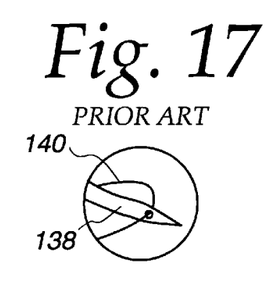
FIG. 17 is an enlarged, fragmentary view of a thread holding portion on the instrument in FIG. 15.
Figure 18:
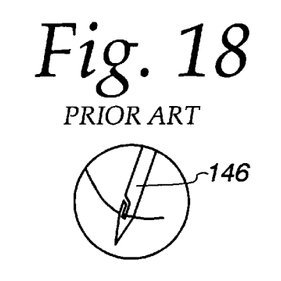
FIG. 18 is a view as in FIG. 17 of the thread holding portion on the instrument in FIG. 16.

Once the particular procedure is completed, the caps 120, 122 can be loosened to release the threads 112, 124 from the connecting arms 106, 108. The bladder 103 can then be deflated, allowing the cannula 102 and device/sealing element 18 to be separated from the tissue 14. The ends 114, 116, 126, 128 of the threads 112, 124 remain conveniently externally of the tissue 14 to be tied to each other in a manner to close the opening 16. The thread ends 114, 116, 126, 128 can be tied to each other in a variety of different manners to close the opening 16 beneath the skin layer 84. For example, the thread parts 114, 116 can be tied together as can the thread parts 126, 128, as shown in FIG. 8. Once combined, the thread parts 114, 116 and 126, 128 can be tied to each other as seen in FIG. 8. Alternatively, only the thread parts 114, 116 and the thread parts 126, 128 can be tied as in FIG. 7, or only the thread parts 116, 126 and 114, 124 can be tied. After the underlying tissue layers are closed, the skin 84 can be stapled or sutured to complete the procedure.

To prevent communication of pneumoperitoneum gas from the cavity 12 to externally of the tissue 14, a resilient seal/sleeve 130 (FIG. 9) can be provided in each of the passageways 60, 62, 64, 66 to closely embrace the tying instruments 67, 68 in the event that the body 30 is made from metal. Alternatively, the entire body, or a substantial portion thereof can be made from a sealing rubber material through which the passageways 60, 62, 64, 66 are formed.

Figure 19:
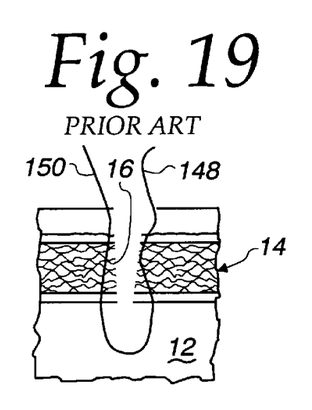
FIG. 19 is a cross-sectional view of a tissue wherein the thread is directed through the tissue into the cavity and outwardly from the cavity through the tissue around a tissue opening through the procedures shown in FIGS. 15 and 16.
Figure 20:
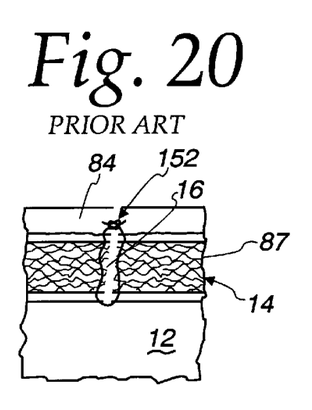
FIG. 20 is a view as in FIG. 19 with the thread tied to close the opening through the tissue.
Figure 21:
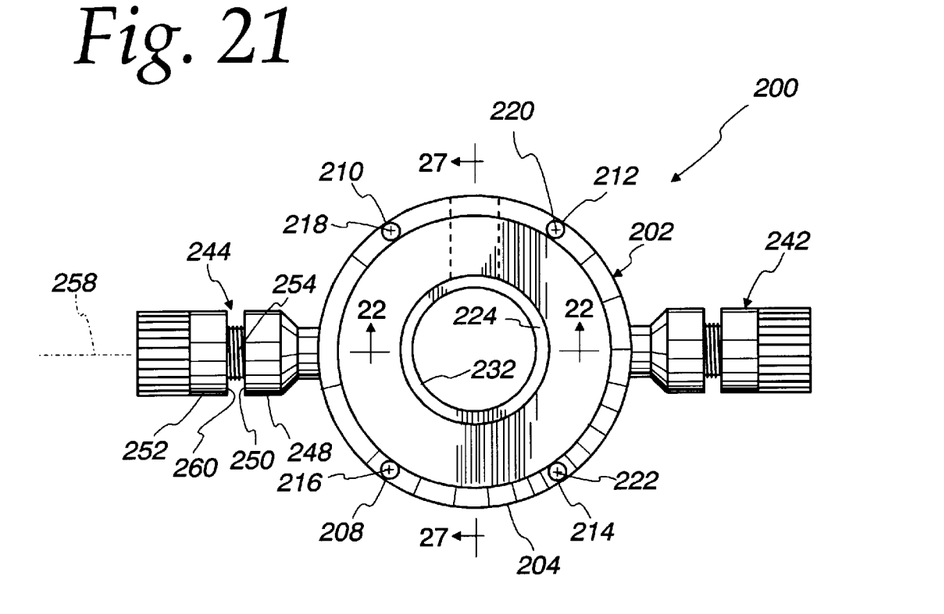
FIG. 21 is a plan view of a modified form of device/sealing element, according to the present invention.

In FIGS. 15–20, a conventional method of closing an opening 16 in tissue 14 is shown. A first instrument 136 having a working end 138 to accept a thread 140 is directed through the tissue 14 adjacent to an operatively set up cannula 142. A second instrument 144 with a slotted working end 146 is directed through the tissue into the cavity 12 to pick up the leading end 148 of the thread 140 and is withdrawn to situate the leading end 148 externally of the tissue 14 adjacent to the trailing end 150 of the thread 140. The ends 148, 150 can then be tied at 152, as shown in FIGS. 19 and 20. A jawed instrument 154 can be directed into the cavity 12 to assist the transfer of the leading thread end 140 from the instrument 136 to the instrument 144. The thread 140 is not used to stabilize the cannula 142. Additionally, the upper tissue layer 84 must be peeled back to allow direction of the thread 140 into the underlying layers 87. Further, to avoid clashing between the instruments 136, 144 and the cannula 142, the thread may have to be directed through the tissue 14 at a greater than desired distance from the tissue opening 16.

In FIGS. 21–27, another system, according to the present invention, is shown at 200, for performing a procedure within the cavity 12 bounded by the tissue 14 with a modified form of device/sealing element 202. The device/sealing element 202 is constructed so that the device/sealing element 202 can be stably maintained upon the tissue 14 in the operative state of FIGS. 23–25 without the need of the inflatable bladder 103, as previously described. Of course, for additional stability, a bladder, or other type of stabilizing element, could be used in conjunction with the device/sealing element 202 having the construction shown in FIGS. 21–27.

The device/sealing element 202 has a body 204 having the same overall configuration as the body 30, previously described, to include a conical, external sealing surface 206, which is borne against the tissue 14 at the opening 16 through the tissue 14. The body 204 has openings/passageways 208, 210, 212, 214 therethrough corresponding to the passageways 60, 62, 64, 66 through the body 30, as previously described. The passageways 208,210,212,214 have central axes 216, 218, 220, 222, consecutively. With this configuration, the passageways 210, 212 and 208, 214 cross between the top 224 and bottom 226 of the body 204. The manner of using the passageways 208, 210, 212, 214 to accommodate a tying instrument 228 is the same as previously described for the device/sealing element 18, previously described. For example, a tying instrument 228 can be used to direct a suturing thread 230 through the passageway 212 in the body 204 and through the tissue 14 to be picked up in the cavity 12 and drawn outwardly through the passageway 210. The suturing thread 230 can be similarly manipulated through the passageways 208, 214. The suturing thread 230 can be directed downwardly through any one passageway 208, 210, 212, 214 and the tissue 14 to be drawn outwardly from the cavity 12 through any one of the other passageways 208, 210, 212, 214.

With the device/sealing element 202 in the operative state, the suturing thread 230 penetrates the tissue 14 below the outer skin layer 87. As in the prior embodiment, preferably the passageways 208, 210, 212, 214 do not intersect the opening 232 through the body 204 defining the passageway for a sleeve/cannula 234 that accommodates a medical instrument 236. For purposes of this disclosure, the sleeve/cannula 234 and medical instrument 236 will cooperatively be described hereinbelow as a medical instrument 238. It is possible that a medical instrument could be constructed to cooperate with the device/sealing element 202 without the need for a separate sleeve/cannula 234. The medical instrument 236 can be any type of instrument useable to perform an operation within the cavity 12.

Figure 22:
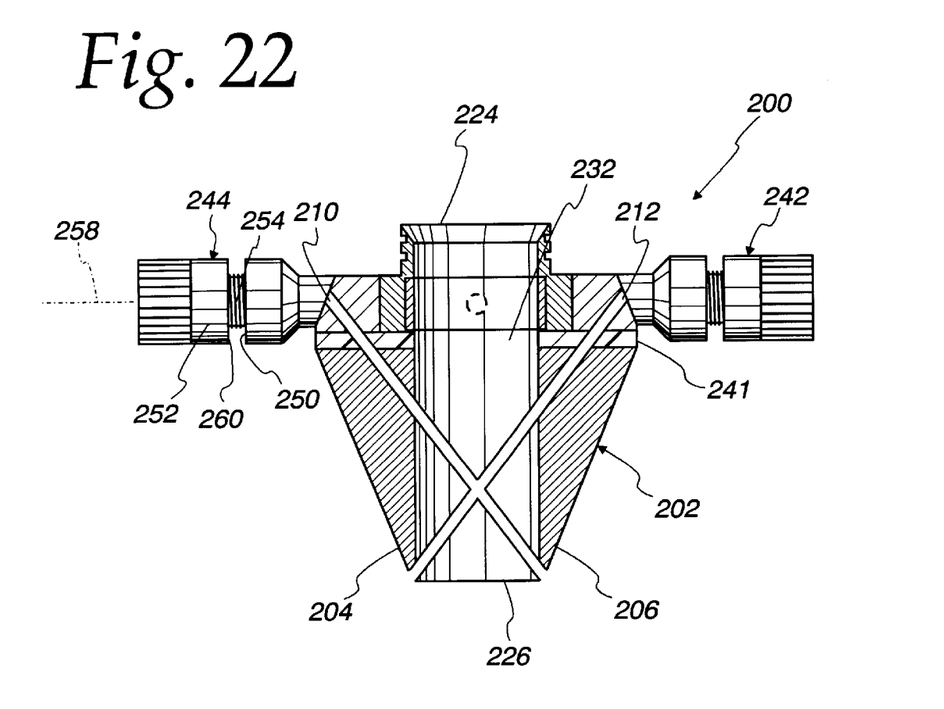
FIG. 22 is a cross-sectional view of the device/sealing element taken along line 22—22 of FIG. 21.
Figure 23:
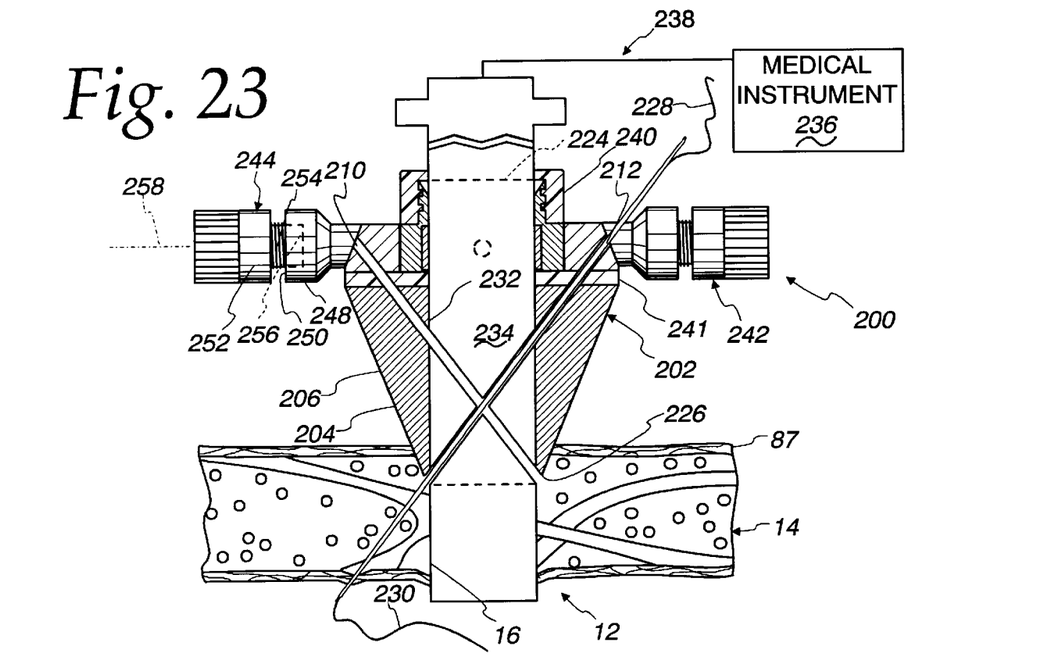
FIG. 23 is a view as in FIG. 22 with the device/sealing element in an operative state with respect to tissue and with suturing thread being manipulated through the device/sealing element and tissue from externally of the cavity bounded by the tissue.
Figure 24:
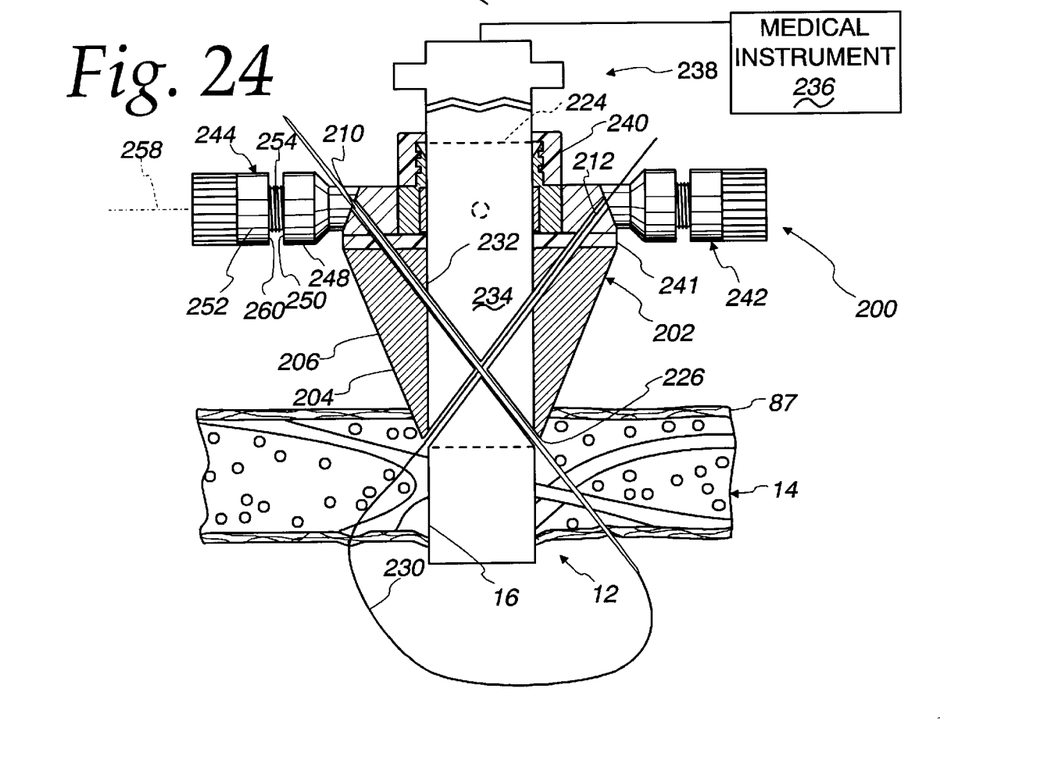
FIG. 24 is a view as in FIG. 23 with the suturing thread directed through the tissue being drawn outwardly from the tissue.

A gasket 240 at the top of the body 204 provides a seal for the sleeve/cannula 234. A sealing layer 240 is provided between the top 224 and bottom 226 of the body 204 and seals around the tying instrument 228 extending through any of the passageways 208, 210, 212, 214 and the sleeve/cannula 234.

Figure 25:
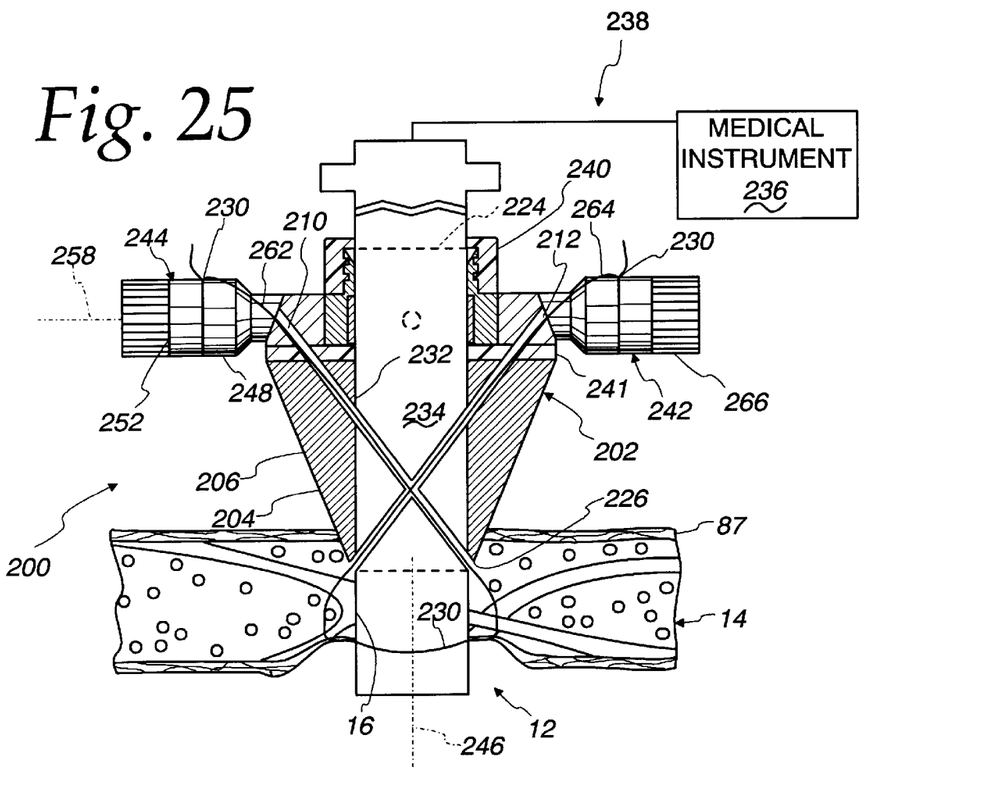
FIG. 25 is a view as in FIGS. 23 and 24 with the ends of the suturing thread being held by the device/sealing element to stabilize the device/sealing element relative to the tissue.
Figure 26:
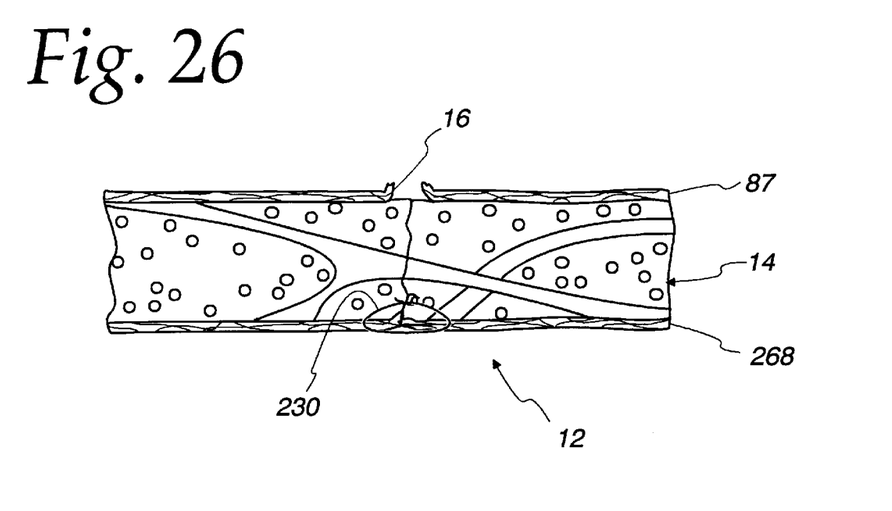
FIG. 26 is a cross-sectional view of the tissue in FIGS. 23–25 with the device/sealing element removed and a knot being formed around an opening through the tissue.

The suturing thread 230 can be used to initially stabilize the device/sealing element 202 in the operative state upon a tissue 14, and thereafter can be used to close the tissue opening 16, as previously described. In this embodiment, the body 204 has cantilevered arms 242, 244 projecting diametrically oppositely from the central axis 246 of the opening 232 defining the passageway for the medical instrument 238. Since both arms 242, 244 have the same construction, the details of only exemplary arm 244 will be discussed. The arm 244 has a fixed portion 248 defining a first flat surface 250. A repositionable element/cap 252 has a threaded stem 254 which mates with a threaded, blind bore 256 in the fixed arm portion 248. By pivoting the repositionable element 252 about an axis 258, the repositionable element 252 can be changed from a first position, as shown in FIGS. 21–24, wherein a flat surface 260 on the repositionable element 252 is spaced from the surface 250 a distance substantially greater than the diameter of the suturing thread 230, and a second position, shown in FIG. 25, wherein the surfaces 252, 260 either abut or are in sufficiently close proximity to captively maintain the suturing thread 230 in a holding position, as shown in FIG. 25.

With this arrangement, a length of suturing thread 230 can be directed downwardly through one passageway 208, 210, 212, 214 and upwardly through another passageway 208, 210, 212, 214 thereby extending under a portion of the underside of the tissue 14. Exposed thread portions 262, 264 can be captively held by the repositionable element 252 on the arm 242 and a corresponding repositionable element 266 on the arm 242.

The arms 242, 244 are preferably formed together with the sealing surface as a unitary structure. In one preferred form, the arms 242, 244 are formed as one piece with the remainder of the body 204 and are in sufficiently close proximity to the bottom 226 of the body 204 to stabilize the device/sealing element 202 upon the tissue 14. Alternatively, the arms 242, 244 could be welded in place.

At the completion of the particular procedure, the device/sealing element 202 can be separated from the tissue 14 by releasing the suturing thread 230 from the arms 242, 244 after loosening the repositionable elements 252, 266. The thread 230 can then be tied, as previously described, to close the incision/opening 16 in the vicinity of the underlying layers 268 thereof.

Figure 27:
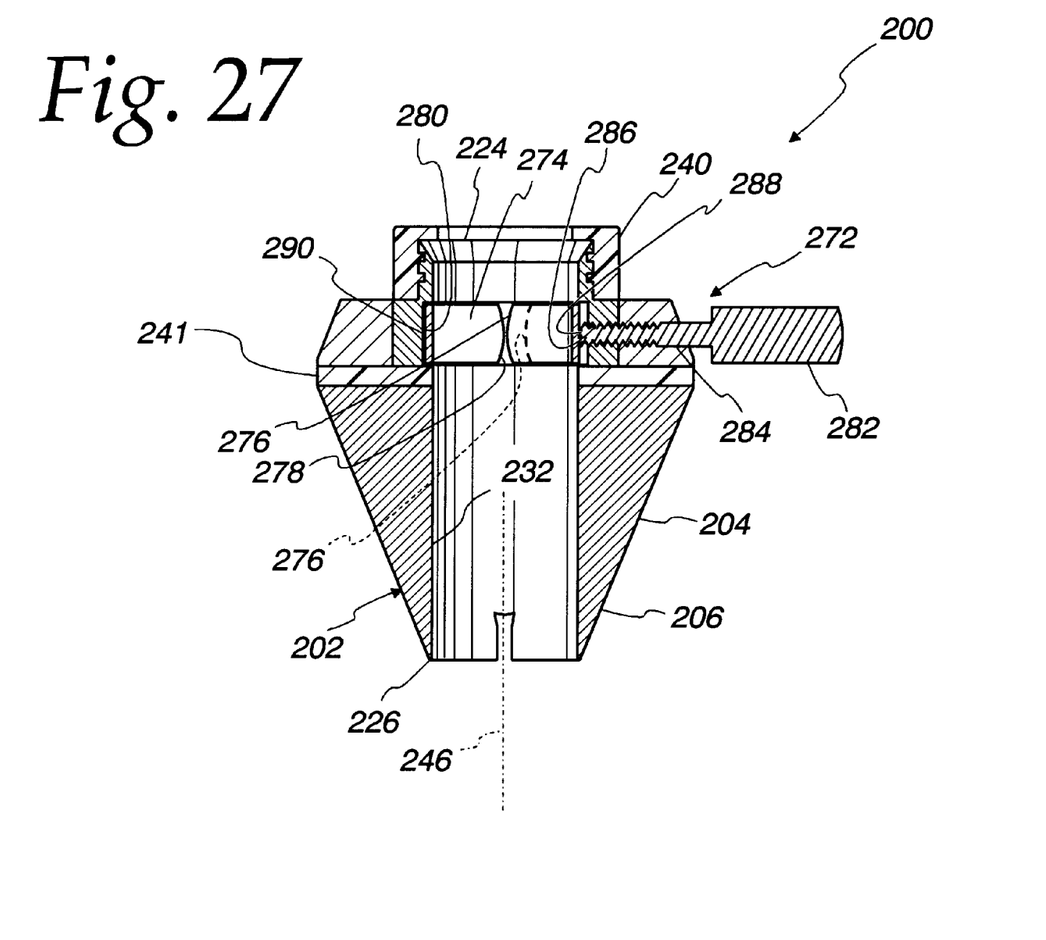
FIG. 27 is a cross-sectional view of the device/sealing element taken along line 27—27 of FIG. 21 with an actuating element in place thereon.

The device/sealing element 202 also includes a releasable locking mechanism, shown at 272 in FIG. 27. The locking mechanism 272 includes a ring member 274 which extends partially around the opening/passageway 232 and diectly bounds a portion thereof. The ring member 274 has spaced, circumferential ends 276, 278. The ring member 274 is reconfigurable to have a variable diameter. In the solid line position of FIG. 27, the ends 276, 278 are in close proximity with the ring member 274 thereby defining a first diameter. With the ends 276, 278 moved away from each other, as shown with the end 278 in phantom lines, the ring member 274 assumes a larger diameter which allows a medical instrument 238 to be slid guidingly along the axis 246 relative to the device/sealing element 202. The ring member 274 nests in a radial, annular undercut 280. The ring member 274 normally assumes the state wherein it has the second effective diameter and resides within the undercut so as not to significantly obstruct the opening/passageway 232.

To reduce the effective diameter of the ring member 274, a repositionable actuator 282 is provided. The actuator 282 has a threaded stem 284 which mates within a threaded bore 286 through the body 204. With this arrangement, the free, leading end 288 of the stem 284 abuts to the outer surface 290 of the ring member 274. As the stem 284 advances radially inwardly towards the axis 246, the ring member 274 is constricted and thereby tends toward the first effective diameter, which thereby causes the ring member 274 to positively embrace the medical instrument 238, thereby fixing the relative position of the body 204 and medical instrument 238.

With the device/sealing element 202, the device/sealing element 202 can be placed in the operative state on the tissue 14 without the need of a bladder or other element within the cavity 12 to abut to the tissue 14 from the underside thereof. The suturing thread 230 can be used to stabilize the device/sealing element 202 and, upon separation of the suturing thread 230 from the device/sealing element 202, closure of the tissue incision/opening 16 using the same suturing thread 230 is facilitated.

The foregoing disclosure of specific embodiments is intended to be illustrative of the broad concepts comprehended by the invention.

I claim:

1. A device for facilitating the performance of a medical procedure in a cavity bounded by a tissue, said device comprising:

a body having a first opening therethrough to define a first passageway for a medical instrument to be directed from externally of the cavity through an opening in the tissue to the cavity and an exposed surface that can be placed against the tissue around the opening therethrough with the device in an operative state relative to the tissue, there being a second opening through the body to define a second passageway through which a tying instrument can be directed from externally of the tissue through the body and into the cavity bounded by the tissue; and a first repositionable element that is movable between first and second positions relative to the body, the first repositionable element in the first position allowing a suturing thread to be placed into and removed from a holding position, the first repositionable element in the second position situated to captively maintain a suturing thread in the holding position.

2. The device for facilitating the performance of a medical procedure according to claim 1 wherein the first repositionable element is threaded and pivotable about an axis in changing between the first and second positions.

3. The device for facilitating the performance of a medical procedure according to claim 2 wherein the body has a first cantilevered arm defining a first surface, the first repositionable element has a second surface, the first and second surfaces are spaced from each other a first distance with the first repositionable element in the first position and the first and second surfaces are at least one of a) abutted to each other and b) spaced from each other a second distance that is less than the first distance with the first repositionable element in the second position.

4. The device for facilitating the performance of a medical procedure according to claim 3 wherein the body has a second cantilevered arm and a second repositionable element that cooperate with each other in the same manner as the first cantilevered arm and first repositionable element cooperate with each other.

5. The device for facilitating the performance of a medical procedure according to claim 4 wherein the first passageway has a central axis and the first and second cantilevered arms project diametrically oppositely away from the central axis of the first passageway.

6. The device for facilitating the performance of a medical procedure according to claim 1 further comprising a releasable locking mechanism for releasably fixing a medical instrument directed through the first opening relative to the body.

7. The device for facilitating the performance of a medical procedure according to claim 6 wherein the releasable locking mechanism comprises a ring member which extends at least partially around the first opening and bounds at least a part of the first opening.

8. The device for facilitating the performance of a medical procedure according to claim 7 wherein the ring member has an effective diameter, the releasable locking mechanism comprises a repositionable actuator that is movable between third and fourth positions, the ring member has a first effective diameter with the actuator in the third position and a second effective diameter that is less than the first effective diameter with the actuator in the fourth position, the ring member with the second effective diameter capable of closely embracing a medical instrument directed through the first opening.

9. The device for facilitating the performance of a medical procedure according to claim 8 wherein the repositionable actuator is threaded and is pivotable about an axis in changing between the third and fourth positions.

10. The device for facilitating the performance of a medical procedure according to claim 8 wherein with the ring member in the third position, the ring member extends through less than 360° around the first opening.

11. The device for facilitating the performance of a medical procedure according to claim 1 in combination with a medical instrument directed into the first opening in the body.

12. The device for facilitating the performance of a medical procedure according to claim 11 wherein there is a third opening through the body to define a third passageway through which a tying instrument can be directed from externally of the tissue through the body and into the cavity bounded by the tissue.

13. The device for facilitating the performance of a medical procedure according to claim 1 in combination with a suturing thread directed through tissue bounding a cavity and held captively in the holding position by the first repositionable element.

14. The device for facilitating the performance of a medical procedure according to claim 1 further comprising a resilient sealing material and the second opening is formed through the resilient sealing material so that the resilient sealing material is directly exposed at the second opening.

15. The device for facilitating the performance of a medical procedure according to claim 1 wherein the body has a first surface, the first repositionable element has a second surface, the second surface on the first repositionable element captively maintains a suturing thread in the holding position with the repositionable element in the second position, and the exposed surface of the body and the first surface are formed together as a unitary structure.

16. In combination:
   a) a device for facilitating the performance of a medical procedure in a cavity bounded by a tissue, said device comprising:
      a body having a first opening therethrough to define a first passageway and an exposed surface that can be placed against the tissue around the opening therethrough with the device in an operative state relative to the tissue, a second opening;
   b) a medial instrument for performing a procedure within the cavity and directed from externally of the cavity through the first passageway into the cavity; and
   c) a suturing thread extendable through the tissue the body and the second opening and held to the body to at least one of i) stabilize the body relative to the tissue and ii) facilitate tying of the suturing thread.

17. The combination according to claim 16 wherein the suturing thread is releasably held to the body.

18. The combination according to claim 16 further comprising a releasable locking mechanism for releasably fixing the medical instrument directed through the first opening relative to the body.

19. The combination according to claim 18 wherein the releasable locking mechanism comprises a ring member that extends at least partially around the first opening and bounds at least a part of the first opening.

20. The combination according to claim 19 wherein the ring member has an effective diameter, the releasable locking mechanism comprises a repositionable actuator that is movable between third and fourth positions, the ring member has a first effective diameter with the actuator in the third position and a second effective diameter that is less than the first effective diameter with the actuator in the fourth position, the ring member with the second effective diameter closely embracing the medical instrument directed through the first opening.

21. The combination according to claim 18 wherein the body has a first surface, the releasable locking mechanism comprises an element with a second surface that captively maintains the suturing thread against the first surface and the exposed surface of the body and the first surface are formed together as a unitary structure.

* * * * *